(12) United States Patent
Pierro et al.

(10) Patent No.: US 9,248,252 B2
(45) Date of Patent: Feb. 2, 2016

(54) NEBULIZER MOUTHPIECE FOR REDUCING DRUG LOSS

(71) Applicant: CareFusion 303, Inc., San Diego, CA (US)

(72) Inventors: Brian Pierro, Yorba Linda, CA (US); Khalid Mansour, Corona, CA (US); Christopher Varga, Laguna Hills, CA (US)

(73) Assignee: CareFusion 303, Inc., San Diego, CA (US)

( * ) Notice: Subject to any disclaimer, the term of this patent is extended or adjusted under 35 U.S.C. 154(b) by 356 days.

(21) Appl. No.: 13/720,894

(22) Filed: Dec. 19, 2012

(65) Prior Publication Data

US 2014/0166011 A1 Jun. 19, 2014

(51) Int. Cl.
| | |
|---|---|
| *A61M 16/14* | (2006.01) |
| *A61M 16/00* | (2006.01) |
| *A61M 11/02* | (2006.01) |
| *A61M 11/06* | (2006.01) |

(Continued)

(52) U.S. Cl.
CPC .............. *A61M 16/14* (2013.01); *A61M 11/02* (2013.01); *A61M 11/06* (2013.01); *A61M 15/0021* (2014.02); *A61M 16/0057* (2013.01); *A61M 16/0825* (2014.02); *A61M 16/0063* (2014.02); *A61M 2202/025* (2013.01); *A61M 2202/0208* (2013.01)

(58) Field of Classification Search
CPC .......... A61M 11/002; A61M 16/0045; A61M 16/08; A61M 16/0816; A61M 16/0833; Y10S 128/91

USPC ............ 128/200.14, 200.18, 200.21, 202.27, 128/203.18, 204.18, 910
See application file for complete search history.

(56) References Cited

U.S. PATENT DOCUMENTS

| | | | | | |
|---|---|---|---|---|---|
| 3,580,249 | A | * | 5/1971 | Takaoka | A61M 16/125 128/200.14 |
| 4,712,580 | A | * | 12/1987 | Gilman | A61M 16/20 128/204.18 |

(Continued)

FOREIGN PATENT DOCUMENTS

| | | |
|---|---|---|
| EP | 0711609 A2 | 5/1996 |
| WO | WO96/29108 A1 | 9/1996 |

OTHER PUBLICATIONS

International Search Report and Written Opinion in PCT Application No. PCT/US2013/074441 dated Apr. 8, 2014 in 14 pages.

*Primary Examiner* — (Jackie) Tan-Uyen T Ho
*Assistant Examiner* — Joseph D Boecker
(74) *Attorney, Agent, or Firm* — McDermott Will & Emery LLP

(57) ABSTRACT

A method for reducing a loss of medication from a nebulizer includes the steps of entraining a liquid medication into a first flow of a pressurized gas into a nebulizer chamber and also entraining an additional amount of the liquid medication into a second flow of ambient air drawn into the nebulizer chamber through an opening when a patient inhales through the nebulizer chamber. When the patient exhales, a portion of the exhaled breath is directed into the outlet of the nebulizer chamber, thereby increasing a backpressure within the outlet and substantially stopping the second flow of ambient air into the nebulizer chamber, thereby decreasing the amount of medication lost to the ambient environment while the patient is not inhaling.

16 Claims, 5 Drawing Sheets

(51) Int. Cl.
*A61M 16/08* (2006.01)
*A61M 15/00* (2006.01)

(56) References Cited

U.S. PATENT DOCUMENTS

| | | | |
|---|---|---|---|
| 4,834,084 A * | 5/1989 | Walsh | B63C 11/205 |
| | | | 128/201.11 |
| 5,020,532 A * | 6/1991 | Mahoney | A61M 16/20 |
| | | | 128/204.18 |
| 5,429,302 A | 7/1995 | Abbot | |
| 5,813,401 A * | 9/1998 | Radcliff | A61M 16/208 |
| | | | 128/200.14 |
| 8,220,458 B2 * | 7/2012 | Landis | A61M 16/0816 |
| | | | 128/200.26 |
| 8,439,035 B2 * | 5/2013 | Dantanarayana | A61B 5/0876 |
| | | | 128/203.11 |
| 2005/0252509 A1 | 11/2005 | Rustad et al. | |
| 2007/0230927 A1 * | 10/2007 | Kramer | A61M 16/109 |
| | | | 392/403 |
| 2013/0081616 A1 * | 4/2013 | Tatkov | A61M 16/04 |
| | | | 128/201.13 |

* cited by examiner

NEBULIZER MOUTHPIECE FOR REDUCING DRUG LOSS

CROSS-REFERENCE TO RELATED APPLICATIONS

Not applicable.

BACKGROUND

1. Field

The present invention generally relates to nebulizers and, in particular, to the breathing devices used with a nebulizer dispenser.

2. Description of the Related Art

Medications for certain respiratory conditions, such as asthma and chronic obstructive pulmonary disease (COPD), are often administered as an inhaled aerosol to improve delivery of the medication to the lungs. A nebulizer, also referred to as a "nebuliser," is a medical device which uses mechanical energy to transform a liquid medication into an aerosol. A nebulizer may use compressed gas forced through a nozzle to break up the liquid medication into tiny globules or may use ultrasonic or vibrating-mesh mechanisms to mechanically generate the tiny globules of liquid medication, thereby forming an aerosol mist.

Nebulizers are available in various sizes, including table-top units that are plugged into an electrical outlet, such as shown in FIG. 1. The aerosol mist is delivered to the patient through a breathing element such as a mask, a nasal piece, or a mouthpiece that fits into the mouth.

Conventional designs for nebulizer dispensers produce a continuous flow of the aerosol mist irrespective of whether the patient is inhaling, exhaling, or not breathing on the device at all. One problem with conventional designs is that the aerosolized medication is only delivered to the patient while the patient is inhaling through the breathing device, with the aerosol mist that is generated while the patient is exhaling or not breathing through the device being lost to the ambient atmosphere.

SUMMARY

The disclosed nebulizer dispenser reduces the amount of the aerosolized medication that is not delivered to the patient.

A breathing element is disclosed here that reduces the amount of aerosolized medication that is lost during exhalation by the patient. The breathing element includes an inhalation tube adapted to be held in a patient's mouth such that the patient breathes through the breathing element. Aerosolized medication is carried in a flow of gas provided through a medicine input tube from a nebulizer chamber that contains a liquid medication and aerosolizes the liquid medication. The breathing element also includes an internal baffle at the inner end of the medicine input tube that directs the flow of the aerosolized medication toward the inhalation tube during an inhalation by the patient. During an exhalation by the patient, the baffle redirects a portion of the exhaled gas into the medicine input tube, thereby slowing the flow rate of the gas carrying the aerosolized medication during the exhalation.

In certain embodiments, a method for reducing a loss of medication from a nebulizer is disclosed. The method includes the steps of entraining a liquid medication into a first flow of a pressurized gas into an interior volume of a nebulizer chamber, and entraining an additional amount of the liquid medication into a second flow of ambient air into the interior volume through an opening when a patient inhales through the nebulizer chamber such that the patient receives a mixture of the first flow of gas and the second flow of ambient air. The mixture flows out of the interior volume to the patient through an outlet in a first direction. The method also includes the step of directing, when the patient exhales, a portion of an exhaled breath of the patient into the outlet in a second direction opposite to the first direction, thereby increasing a backpressure within the outlet and substantially stopping the second flow of ambient air into the interior volume, thereby decreasing the amount of medication lost to the ambient environment while the patient is not inhaling.

In certain embodiments, a breathing element is disclosed that includes a body comprising a first passage having a first external opening and a first internal end, a shaped baffle disposed within the body and coupled to the internal end of the first passage, a breathing piece coupled to the body and comprising a second passage having a second external opening and a second internal end that is fluidly coupled to the first internal end of the first passage through the shaped baffle, and an exhaust piece coupled to the body and comprising a third passage having a third external opening and a third internal end that is fluidly coupled to the second internal end of the second passage.

In certain embodiments, a nebulizer dispenser is disclosed that includes a nebulizer chamber configured to accept a quantity of a liquid medication and a flow of a gas, aerosolize the liquid medication, and provide a first flow of gas carrying the aerosolized medication. The dispenser also includes a breathing element configured to be coupled to the nebulizer chamber. The breathing element includes a body comprising a first passage having a first external opening and a first internal end. The first passage is configured to accept the first flow of gas from the nebulizer chamber through the first external opening. The breathing element also includes a shaped baffle disposed within the body and coupled to the internal end of the first passage, a breathing piece coupled to the body and comprising a second passage having a second external opening and a second internal end that is fluidly coupled to the first internal end of the first passage through the shaped baffle, and an exhaust piece coupled to the body and comprising a third passage having a third external opening and a third internal end that is fluidly coupled to the second internal end of the second passage.

In certain embodiments, a breathing element is disclosed that includes an inhalation tube, an exhaust tube, a medicine input tube configured to accept a flow of a gas, and a baffle with a first opening fluidically coupled to the medicine input tube and a second opening fluidically coupled to the inhalation tube and the exhaust tube. The baffle provides a free flow of the gas from the medicine input tube to the inhalation tube during an inhalation by a patient through the inhalation tube and redirects a portion of the gas exhaled by the patient through the inhalation tube into the medicine input tube.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed nebulizer dispenser reduces the amount of the aerosolized medication that is not delivered to the patient. In certain embodiments, the nebulizer dispenser includes a shaped flow diverter that diverts a portion of the patient's exhaled gas into the passage through which the flow of aerosolized medication is provided by the medication cup, thereby causing an accumulation of the aerosolized medication within the passage and reducing the amount of aerosolized medication lost during the exhalation.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

Figure 1:
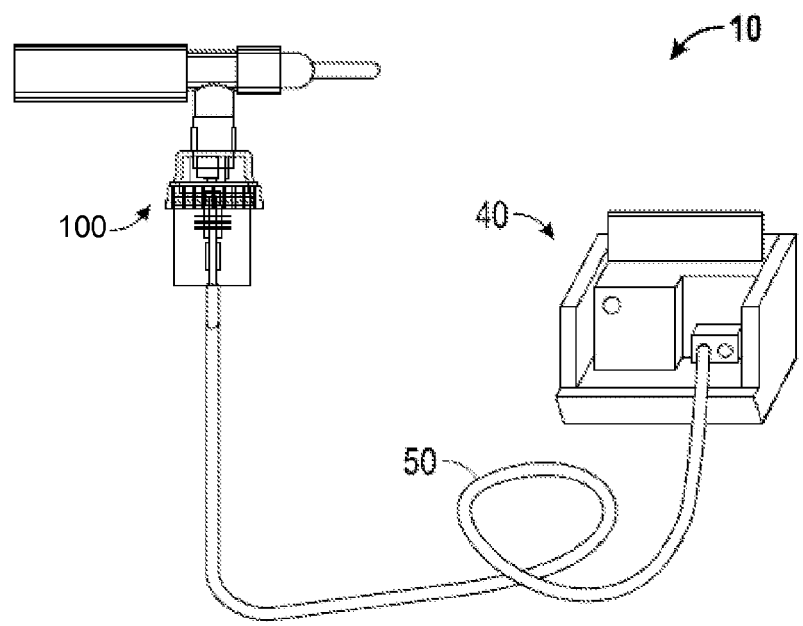
FIG. 1 depicts a nebulizer system according to certain aspects of the present disclosure.

FIG. 1 depicts a nebulizer system according to certain aspects of the present disclosure. The system 10 includes a dispenser 100 connected through tubing 50 to a separate source 40 of pressurized air. The source 40 typically includes an air compressor (not visible in FIG. 1) that compresses ambient air to provide the pressurized air. In a healthcare facility, the pressurized air may be available from a wall fixture (not shown in FIG. 1) and, in this situation, the tubing 50 may be connected to the wall fixture rather than the source 40. Nebulizers may also operate using other gases in place of pure air, for example commercially pure oxygen as typically provided in a healthcare facility, oxygen-enriched air, a helium-oxygen mixture such as heliox, or any other mixture of gases suitable for breathing. In certain embodiments, the dispenser 100 may be integrated into a self-contained handheld nebulizer (not shown in FIG. 1) that includes a power source, such as a battery, and a source of compressed air, such as an air pump.

Figure 2:
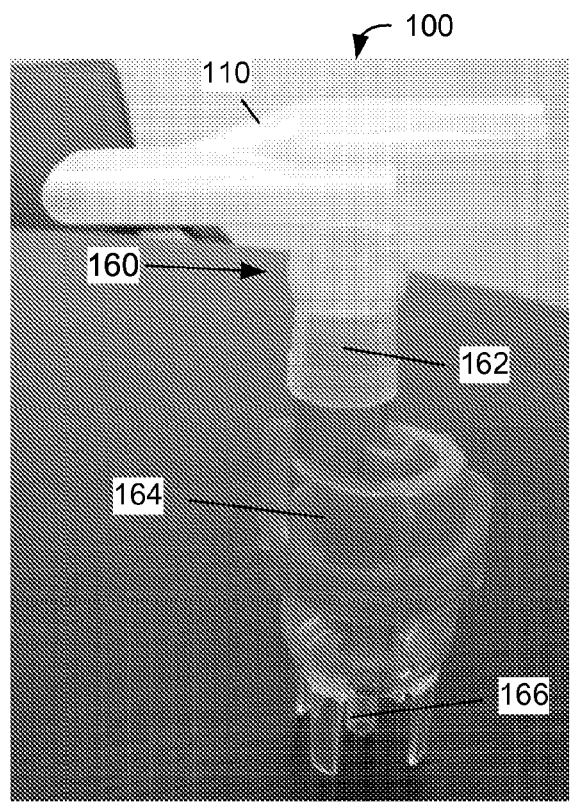
FIG. 2 depicts a nebulizer dispenser according to certain aspects of the present disclosure.

FIG. 2 depicts a nebulizer dispenser 100 according to certain aspects of the present disclosure. The dispenser 100 includes, in this embodiment, a breathing element 110 that is connected through a ball-and-socket joint 160 to an adapter 162 that is then connected to a nebulizer chamber 164, also referred to as a "medicine cup." In certain embodiments, the adapter 162 is integrated with the nebulizer chamber 164. Details of the ball-and-socket 160 are described in a related application Ser. No. 13/720,877, filed on the same day as this application and incorporated in its entirely by reference. However, although a ball-and-socket 160 are depicted herein, conventional arrangements for connecting a breathing element to a nebulizer chamber 164.

A liquid medication, or other therapeutic liquid, is introduced into the nebulizer chamber 164 and a source of compressed gas (not shown in FIG. 2), delivered via tubing 50, is connected to an inlet 166 of the nebulizer chamber 164. The pressurized gas entering the nebulizer chamber 164 entrains the liquid medication and disperses the entrained liquid medication as flow of an aerosolized mist that is delivered through the breathing element 110 to the patient. In certain embodiments, the nebulizer chamber 164 may include a venturi (not visible in FIG. 2) to aid in the entrainment of the liquid medication. In certain embodiments, the nebulizer chamber 164 may include a mechanism (not visible in FIG. 2) to mechanically generate droplets of the liquid medication. In certain embodiments, the nebulizer chamber 164 may include other devices and systems to aerosolize the liquid medication and provide the aerosolized medication as part of a gas flow provided to the breathing element 110.

Figure 3:
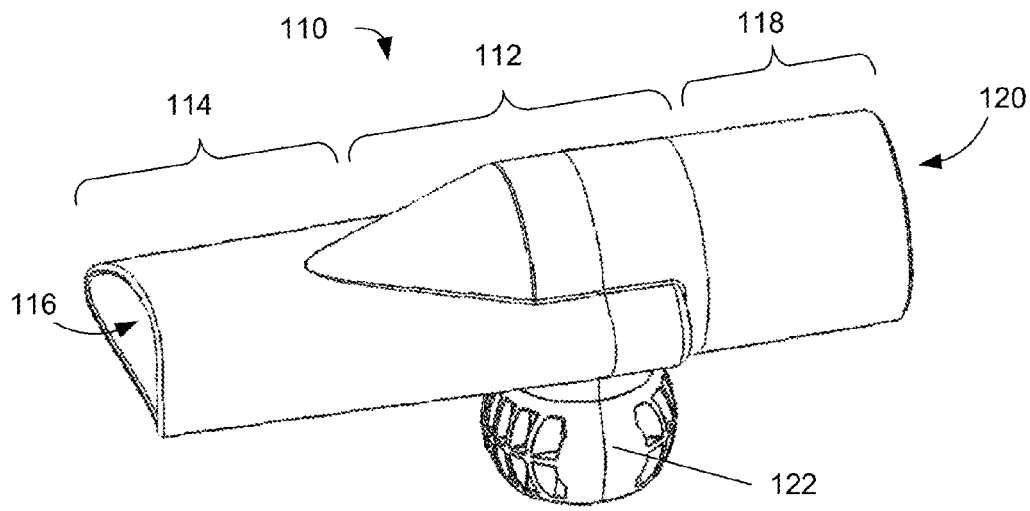
FIG. 3 depicts an exemplary embodiment of a breathing element according to certain aspects of the present disclosure.

FIG. 3 depicts an exemplary embodiment of a breathing element 110 according to certain aspects of the present disclosure. The example embodiment shown in FIG. 3 has a body portion 112 integrally formed with a breathing piece 114 and an exhaust piece 118. The breathing piece 114 is arranged to be placed in the mouth of a patient such that a flow of gas through the passage 116 will enter the patient's mouth. The exhaust piece 118 has a passage 120 having an interior end that is coupled to an interior end of the passage 116, and exhaled gas passes from passage 116 through passage 120 to the ambient atmosphere. The flow paths through the breathing element 110 are discussed in greater detail with respect to FIGS. 4B and 4C. In this embodiment, a ball 122 is coupled to the body portion 112 and is configured to form a part of the ball-and-socket joint 160. In certain embodiments, one or both of the breathing piece 114 and the exhaust piece 118 may be separately formed and coupled, either permanently or removably, to the body portion 112. It should be noted that the disclosed breathing element 110 may be formed as a single piece or as multiple pieces that are then assembled to provide the same features without departing from the scope of this disclosure.

Figure 4A:
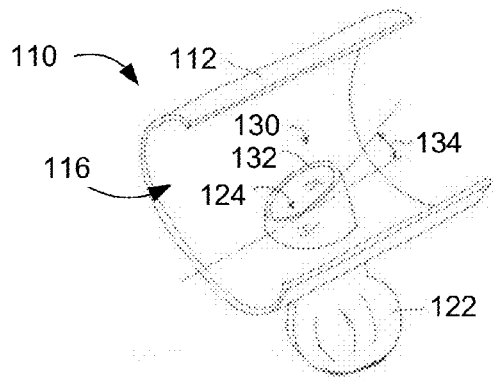
FIG. 4A is a cutaway view of a portion of the breathing element of FIG. 3 showing an example baffle according to certain aspects of the present disclosure.
Figure 8:
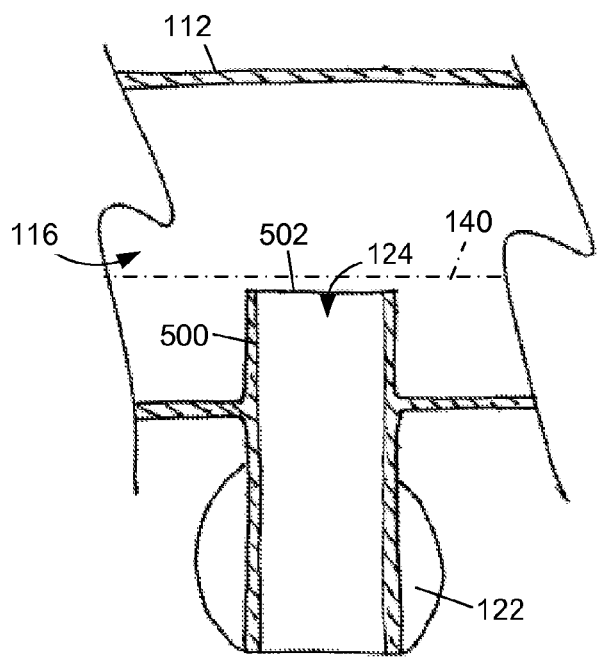
FIG. 8 is another embodiment of a shaped baffle according to certain aspects of the present disclosure.

FIG. 4A is a cutaway view of a portion of the breathing element 110 of FIG. 3 showing an example baffle 130 according to certain aspects of the present disclosure. The shaped baffle 130 is coupled between the interior ends of passages 116 and 124 and that, in this embodiment, has the general shape of a truncated cone. In certain other embodiments, the shaped baffle 130 may have the general shape of a cylinder, as shown in FIG. 8. In certain embodiments, the baffle 130 is disposed within the body 112 and may protrude into the passage 116. The baffle 130 may have a sloped top plane 132.

Figure 4B:
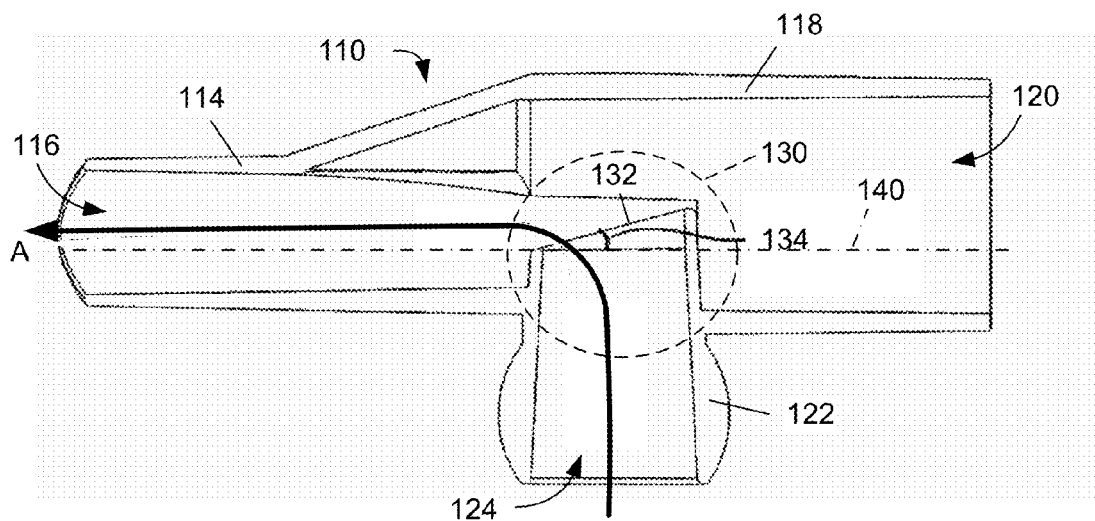
FIGS. 4B-4C are cross-sections of the breathing element of FIG. 3 showing the directions of flow according to certain aspects of the present disclosure.
Figure 4C:
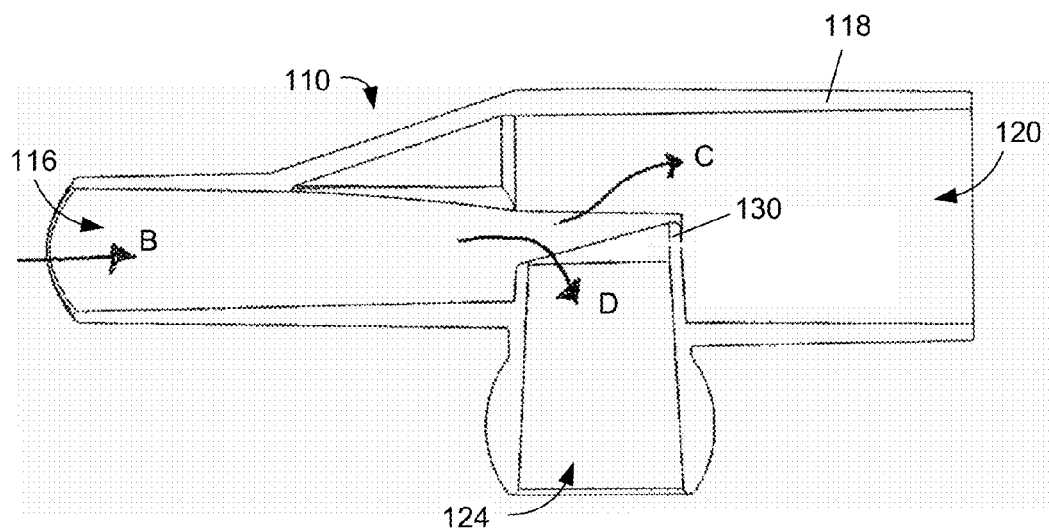

FIGS. 4B-4C are cross-sections of the breathing element 110 of FIG. 3 showing the directions of flow according to certain aspects of the present disclosure. FIG. 4B depicts the flow of the aerosolized medication during an inhalation by the patient. An interior end of passage 116 is coupled to an interior end of a passage 124 and an interior end of passage 120 is coupled to the interior end of a passage 116. As the patient inhales, the pressure within the passage 116 is reduced while, at the same time, the delivery of the pressurized gas flow carrying the aerosolized medication raises the pressure, relative to ambient air pressure, within the passage 124 within the ball 122. This pressure gradient causes the delivered aerosolized medication to flow generally entirely from the passage 124 to the passage 116, as indicated by the arrow "A," and therethrough to the patient. In certain embodiments, there are no other flow control elements, e.g. a flapper or other one-way valve, included in any of the passages 116, 120, and 124.

The sloped top plane 132 of baffle 130 may be formed at an angle 134 relative to a reference axis 140. In general, the angle 134 may be in the range of 0-90° with respect to the reference axis 140. In certain embodiments, the angle 134 may be in the range of 2-45° and, in certain embodiments, the angle 134 may be in the range of 15-30°. The baffle creates a partial blockage of the connection between the passage 120 of the exhaust piece 118 and the passage 116. As the pressure within the passage 120 is at atmospheric pressure, and therefore above the pressure in passage 116 during inhalation, there may be a relatively small flow of ambient air through the passage 120 into passage 116 during inhalation. The combination of the baffle 130 and the higher pressure within the passage 124, compared to ambient air pressure, may tend to induce a preferential flow to the passage 116 from the passage 124 rather than from passage 120. It should be noted that a similar baffle 130 may be provided in other types of breathing elements, such as masks, with similar effect and benefit.

FIG. 4C shows the gas flow during an exhalation by the patient. The patient blows the exhaled gas at a slightly elevated pressure, compared to ambient pressure, into passage 116, as indicated by arrow "B." A portion of the exhaled gas flow may be diverted toward the passage 124 by the baffle 130, as indicated by arrow "D," while the remainder of the gas flow will flow out through the passage 120 to the ambient atmosphere, as indicated by arrow "C." During exhalation, the nebulizer body 164 is still providing a flow of pressurized gas carrying the aerosolized medication into the bottom of passage 124 and any aerosolized medication that enters the passage 116 will be diverted out through the passage 120 and wasted. However, the flow "D" of the exhaled gas flow into the top of the passage 124 creates an increase in the pressure within the passage 124, compared to what the pressure would be during exhalation within passage 124 if there was no baffle 130. Accordingly, with baffle 130, the flow rate of the aerosolized medication from the passage 124 into the passage 116 during exhalation is reduced.

The increased pressure within the passage 124 and the upstream flow path from the nebulizer chamber 164 effectively accumulates some of the aerosolized medication that would have otherwise been wasted. After the patient completes an exhalation and starts the next inhalation, the increased pressure within the passage 124 will cause a slight surge in the flow rate from the passage 124 into the passage 116 and deliver this accumulated medication to the patient. Thus, a portion of the aerosolized medication that would have been lost to the ambient atmosphere in a conventional breathing element will be accumulated and delivered to the patient by the disclosed breathing element 110.

Figure 5A:
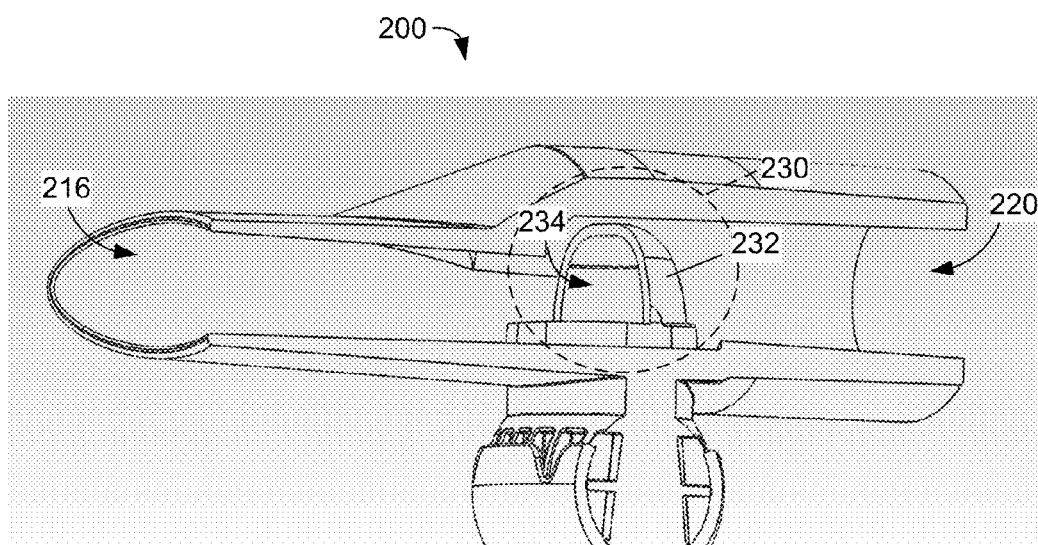
FIG. 5A is a cutaway view of another embodiment of a breathing element according to certain aspects of the present disclosure.

FIG. 5A is a cutaway view of another embodiment 200 of a breathing element according to certain aspects of the present disclosure. In this embodiment, the shaped baffle 230 is provided as a generally spherical half-dome 232 with an open side 234 facing toward the passage 216. In certain embodiments, there are no other flow control elements, e.g. a flapper or other one-way valve, included in the passages 216 and 220 or other gas flow passages within the breathing element 200.

Figure 5B:
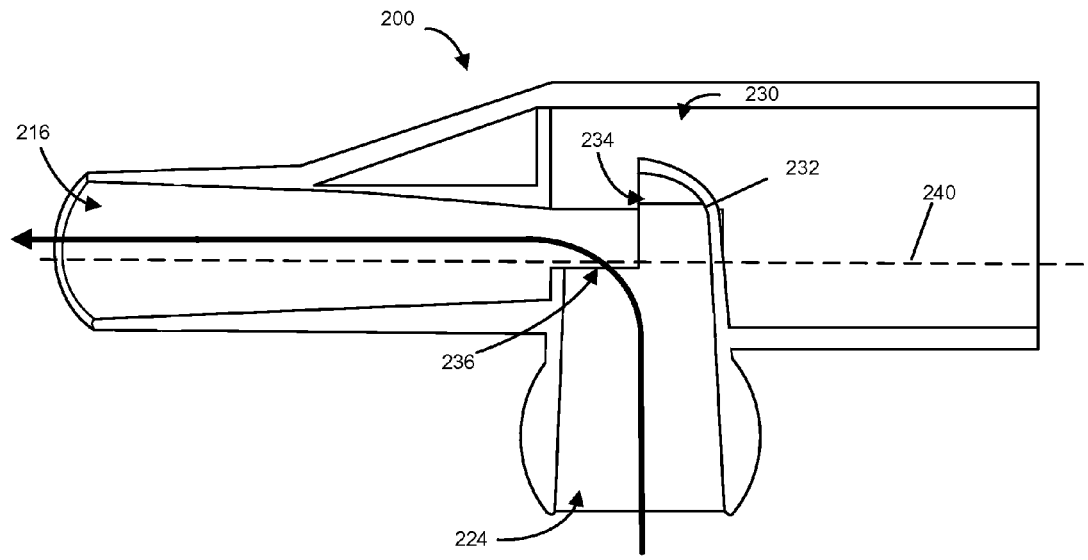
FIG. 5B is a cross-section of the breathing element of FIG. 5A according to certain aspects of the present disclosure.

FIG. 5B is a cross-section of the breathing element 200 of FIG. 5A according to certain aspects of the present disclosure. The open side 234 of the half-dome 232 is seen in profile, with the remainder of the opening of the passage 224 into the passage 216 having a top plane 236 that, in certain embodiments, is parallel to an axis 240. In certain embodiments, the top plane 236 may have an angle, similar to the angle 134 of FIG. 4B, in the range of 45-90° with respect to the reference axis 240. The vertical open face 234 is effective at diverting a portion of an exhaled breath into the passage 224, thereby causing an increased backpressure within the passage 224 and may accumulate an increased amount of aerosolized medication, compared to the embodiments 110 with small angles 134. In certain embodiments, the open face 234 may be provided at an angle other than vertical. It should be noted that a similar half-dome baffle 230 may be provided in other types of breathing elements, such as masks, with similar effect and benefit.

It should be noted that the shape and configuration of the baffle 130, 230 may be of any shape. e.g. round, oval, rectangular, and such, and may include multiple half-domes or similar shells or a plurality of sub-passages through the baffle that connect the passages 116 and 124. In certain embodiments, the baffle 130, 230 may be at least partially disposed within the passage 124. The passages 116, 120, and 124 and baffle 130, 230 can be arranged in any configuration wherein a patient may inhale a gas provided at an external opening of passage 124 through an external opening of passage 116 and then exhale through the same external opening of passage 116 and have the exhaled gas pass through an external opening of passage 120.

Figure 6:
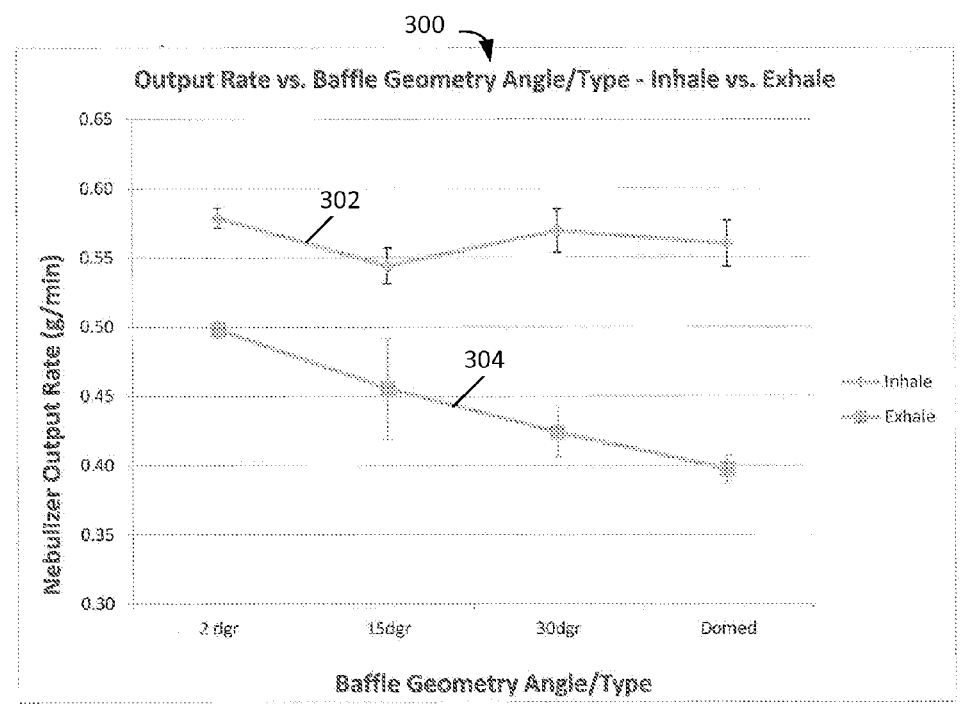
FIG. 6 is a chart showing the output flow rates of an example embodiment of a nebulizer dispenser according to certain aspects of the present disclosure.

FIG. 6 is a chart 300 showing the output flow rates of an example embodiment of a nebulizer dispenser according to certain aspects of the present disclosure. The flow rates of the gas flow from the nebulizer chamber 164 into several embodiments of breathing elements according to this disclosure were measured during inhalation and exhalation. The embodiments that were measured were embodiments 110 as shown in FIG. 4B with angles 134 of 2°, 15°, and 30°, and an embodiment 200 as shown in FIG. 5B with a domed baffle 230. The curve 302 of the flow rates during inhalation are above the curve 304 of the flow rates during exhalation for all embodiments. The difference between the inhalation and exhalation flow rates ranged from 16% for the embodiment 110 with an angle of 2° to 40% for the domed embodiment 200.

Figure 7:
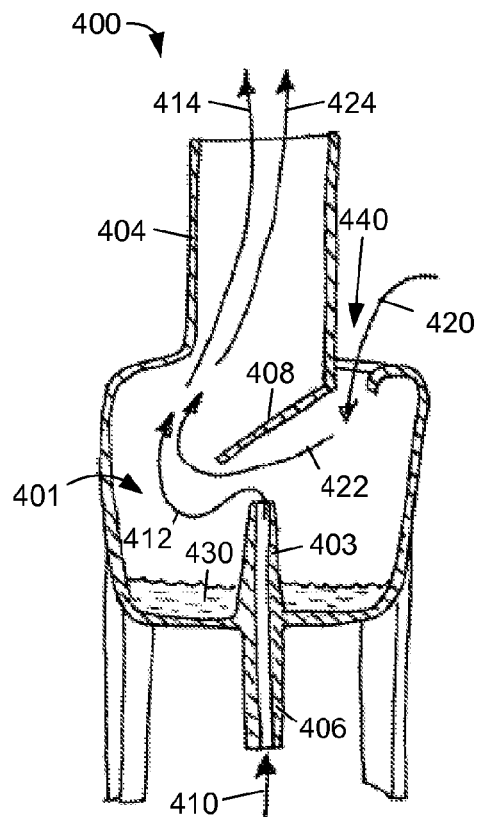
FIG. 7 is an example embodiment of a nebulizer chamber according to certain aspects of the present disclosure.

FIG. 7 is an example embodiment of a nebulizer chamber 400 according to certain aspects of the present disclosure. The nebulizer chamber 400 includes an opening 440 from the ambient environment into the interior volume 401 that contains the medication 430. A flow 410 of pressurized gas enters the inlet 406 and entrains the liquid medication 430 as the flow 410 passes up the tubular projection 403 (the entrainment passages of the tubular projection 403 have been omitted for clarity). There is a baffle 408 that deflects the medication-laden air flow 410 into the interior volume 401 and prevents the air flow that emerges from the tubular projection 403 from flowing directly out of the outlet 404.

During an inhalation cycle, a flow 420 of ambient air is drawn in through the opening 440 and then both the pressurized air flow 410 and ambient air flow 420 mix as they flow through the interior volume 401 as indicated by arrows 412 and 422 and then exit through outlet 404 into a breathing element (not shown in FIG. 7). This embodiment of the nebulizer chamber 400 provides a higher air flow to the patient than is provided by the pressurized air flow 410. As a non-limiting example provided for illustrative purposes, the flow 410 of pressurized air may be constant at 10 standard cubic feet per minute (std cfm). During an inhalation cycle, the flow 420 of ambient air may reach a peak value of 8 std cfm, with the patient inhaling 18 std cfm of the mixture of flows 410 and 420. The air flow 420 decreases and may drop to zero or may even reverse direction during an exhalation cycle. Thus, the patient receives a flow of diluted medication-laden gas, being the sum of flows 414 and 424, that is greater than the flow of medication-laden gas 410 that is provided when the patient is exhaling.

During exhalation there is an increase in backpressure within the outlet 404, induced by the diversion within the breathing element of the patient's exhaled breath into the outlet 404, as previously discussed. As the air flow 420 during the prior inhalation cycle diluted the concentration of the entrained medication in the gas within the interior volume 401, the continued flow 410 of medication-laden gas into the interior volume 401 will tend to displace the diluted gas out of the outlet 404 and also out of the opening 440. As this displaced diluted gas is lost, while the newly introduced medication-laden gas flow 410 tends to be retained within the interior volume 401, the net result is an increase in the amount of entrained medication in the gas within the interior volume 401 and a reduction in the amount of medication lost to the ambient environment.

FIG. 8 is another embodiment of a shaped baffle 500 according to certain aspects of the present disclosure. This embodiment shares many features of the embodiment of FIG. 4B and like features are not described again. In this embodiment, the shaped baffle 500 has a generally cylindrical form and a top plane 502 that is parallel to the reference axis 140. In certain embodiments, this generally cylindrical form may be combined with the half-dome 232 of FIG. 5B or a sloped top surface 132 as shown in FIG. 4B without departing from the scope of this disclosure.

The disclosed examples of nebulizer breathing elements provide a decrease in the amount of aerosolized medication that is lost to the ambient atmosphere and, therefore, an increase in the fraction of a dose of the liquid medication that is delivered to the patient in aerosol form. The internal baffle diverts a portion of the exhaled gas into the passage through which the aerosolized medication enters the breathing element, thereby causing some of the aerosolized medication to accumulate within the breathing element during the exhalation and delivering this accumulated medication to the patient during a subsequent inhalation. This increase in the fraction of the liquid medication that is delivered to the patient may allow a reduction in the amount of liquid medication prescribed for each treatment as well as shortening the treatment time to deliver a certain amount of the medication to the patient in aerosolized form. This shaped baffle may be incorporated into any breathing element, such as a mask, to provide a similar benefit.

This application includes description that is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. It is understood that the specific order or hierarchy of steps or blocks in the processes disclosed is an illustration of exemplary approaches. Based upon design preferences, it is understood that the specific order or hierarchy of steps or blocks in the processes may be rearranged. The accompanying method claims present elements of the various steps in a sample order, and are not meant to be limited to the specific order or hierarchy presented. Thus, the claims are not intended to be limited to the aspects shown herein, but is to be accorded the full scope consistent with the language claims.

Reference to an element in the singular is not intended to mean "one and only one" unless specifically so stated, but rather "one or more." Use of the articles "a" and "an" is to be interpreted as equivalent to the phrase "at least one." Unless specifically stated otherwise, the terms "a set" and "some" refer to one or more.

Terms such as "top," "bottom," "upper," "lower," "left," "right," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Although the relationships among various components are described herein and/or are illustrated as being orthogonal or perpendicular, those components can be arranged in other configurations in some embodiments. For example, the angles formed between the referenced components can be greater or less than 90 degrees in some embodiments.

Although various components are illustrated as being flat and/or straight, those components can have other configurations, such as curved or tapered for example, in some embodiments.

Pronouns in the masculine (e.g., his) include the feminine and neuter gender (e.g., her and its) and vice versa. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "operation for."

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such as an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. A breathing element comprising:
   a body comprising a first passage having a first external opening and a first internal end;
   a shaped baffle disposed within the body and coupled to the first internal end of the first passage, the shaped baffle is configured as a partial-dome comprising a wall that terminates mid-way across the first internal end such that a portion of the first internal end is enclosed by the shaped baffle wall and the remaining portion of the first internal end remains unobstructed;
   a breathing piece coupled to the body and comprising a second passage having a second external opening and a second internal end that is fluidly coupled to the first internal end of the first passage through the shaped baffle; and
   an exhaust piece coupled to the body and comprising a third passage having a third external opening and a third internal end that is fluidly coupled to the second internal end of the second passage;
   wherein the wall of the shaped baffle extends into the second and third passages.

2. The breathing element of claim 1, wherein a portion of a first flow of gas entering the second external opening is diverted into the first passage by the shaped baffle.

3. The breathing element of claim 2, wherein the portion of the first flow of gas that is diverted into the first passage creates an increase in a pressure within the first passage when a second flow of gas is entering the first passage through first external opening.

4. The breathing element of claim 1, wherein the shaped baffle is configured as a cylinder that protrudes into the second passage.

5. The breathing element of claim 1, wherein the shaped baffle is continuously open to flow in both directions.

6. The breathing element of claim 1, wherein the partial-dome comprises a generally spherical portion.

7. The breathing element of claim 1, wherein the partial-dome comprises an open side that faces toward the second passage.

8. The breathing element of claim 7, wherein the open side is at an angle from an axis in the range of 45-90°.

9. A nebulizer dispenser, comprising:
   a nebulizer chamber configured to accept a quantity of a liquid medication and a flow of a gas, aerosolize the liquid medication, and provide a first flow of gas carrying the aerosolized medication; and
   a breathing element configured to be coupled to the nebulizer chamber, the breathing element comprising:
   a body comprising a first passage having a first external opening and a first internal end, wherein the first passage is configured to accept the first flow of gas from the nebulizer chamber through the first external opening;
   a shaped baffle disposed within the body and coupled to the first internal end of the first passage, the shaped baffle is configured as a partial-dome comprising a wall that terminates mid-way across the first internal end such that a portion of the first internal end is enclosed by the shaped baffle wall and the remaining portion of the first internal end remains unobstructed;
   a breathing piece coupled to the body and comprising a second passage having a second external opening and a second internal end that is fluidly coupled to the first internal end of the first passage through the shaped baffle; and
   an exhaust piece coupled to the body and comprising a third passage having a third external opening and a third internal end that is fluidly coupled to the second internal end of the second passage;
   wherein the wall of the shaped baffle extends into the second and third passages.

10. The nebulizer dispenser of claim 9, wherein a portion of a second flow of gas entering the second external opening is diverted into the first passage by the shaped baffle.

11. The nebulizer dispenser of claim 10, wherein the portion of the second flow of gas that is diverted into the first passage creates an increase in a pressure within the first passage when the first flow of gas is entering the first passage through first external opening.

12. The nebulizer dispenser of claim 9, wherein the shaped baffle is continuously open to flow in both directions.

13. The nebulizer dispenser of claim 9, wherein the partial-dome comprises a generally spherical portion.

14. The nebulizer dispenser of claim 9, wherein the partial-dome comprises an open side that faces toward the second passage.

15. The nebulizer dispenser of claim 14, wherein the open side is at an angle from an axis generally aligned with the second passage, the angle being in the range of 45-90°.

16. A breathing element, comprising:
    an inhalation tube;
    an exhaust tube;
    a medicine input tube configured to accept a flow of a gas; and
    a baffle with a first opening fluidically coupled to the medicine input tube and a second opening fluidically coupled to the inhalation tube and the exhaust tube, the shaped baffle is configured as a partial-dome comprising a wall that extends into the inhalation tube and the exhaust tube, and terminates mid-way across the first internal end, such that a portion of the medicine input tube is enclosed by the baffle wall and the remaining portion of the medicine input tube remains unobstructed, wherein the baffle provides a free flow of the gas from the medicine input tube to the inhalation tube during an inhalation by a patient through the inhalation tube, and redirects a portion of the gas exhaled by the patient through the inhalation tube into the medicine input tube.

* * * * *